United States Patent
Oura et al.

(10) Patent No.: US 12,251,266 B2
(45) Date of Patent: Mar. 18, 2025

(54) PHYSIOLOGICAL INFORMATION MEASUREMENT APPARATUS AND PHYSIOLOGICAL INFORMATION SYSTEM

(71) Applicant: NIHON KOHDEN CORPORATION, Tokyo (JP)

(72) Inventors: Mitsuhiro Oura, Tokorozawa (JP); Sou Kumagai, Tokorozawa (JP); Wataru Matsuzawa, Tokorozawa (JP); Nobuyuki Yasumaru, Tokorozawa (JP); Kazuya Nagase, Tokorozawa (JP); Hiroshi Torigai, Tokorozawa (JP); Naoki Fukushima, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 780 days.

(21) Appl. No.: 17/266,799

(22) PCT Filed: Jul. 26, 2019

(86) PCT No.: PCT/JP2019/029477
§ 371 (c)(1),
(2) Date: Feb. 8, 2021

(87) PCT Pub. No.: WO2020/031756
PCT Pub. Date: Feb. 13, 2020

(65) Prior Publication Data
US 2021/0315542 A1    Oct. 14, 2021

(30) Foreign Application Priority Data

Aug. 9, 2018 (JP) ................................. 2018-149817

(51) Int. Cl.
*A61B 8/00* (2006.01)
*G01S 7/52* (2006.01)
(Continued)

(52) U.S. Cl.
CPC .......... *A61B 8/463* (2013.01); *G01S 7/52053* (2013.01); *G01S 15/8906* (2013.01);
(Continued)

(58) Field of Classification Search
CPC ........... A61B 8/463; A61B 5/01; A61B 5/021; A61B 5/024; A61B 5/0816;
(Continued)

(56) References Cited

U.S. PATENT DOCUMENTS

2003/0163045 A1   8/2003  Gatzke
2004/0249279 A1  12/2004  Maschke
(Continued)

FOREIGN PATENT DOCUMENTS

JP   2007282792 A  * 11/2007
JP   2011-139896 A    7/2011
(Continued)

OTHER PUBLICATIONS

International Search Report dated Oct. 18, 2019 issued by the International Searching Authority in counterpart International Application No. PCT/JP2019/029477 (PCT/ISA/210).
(Continued)

*Primary Examiner* — Chao Sheng
(74) *Attorney, Agent, or Firm* — Sughrue Mion, PLLC

(57) ABSTRACT

A physiological information measurement apparatus is configured to acquire a vital sign that is based on a physiological signal of a subject, and a captured image or a signal for generating the captured image that is acquired from an imaging device. The physiological information measurement apparatus includes a storage unit configured to store therein an electronic file, and a control unit configured to display at least one of the captured image and information of the vital sign on a display unit. At an image recording timing when an image recording instruction is provided, the control
(Continued)

unit stores both the captured image and the information of the vital sign in the storage unit in an image format.

16 Claims, 13 Drawing Sheets

(51) Int. Cl.
| | |
|---|---|
| *G01S 15/89* | (2006.01) |
| *G06F 16/51* | (2019.01) |
| *G16H 10/60* | (2018.01) |
| *G16H 15/00* | (2018.01) |
| *G16H 30/20* | (2018.01) |
| *G16H 30/40* | (2018.01) |
| *G16H 40/63* | (2018.01) |
| *G16H 50/30* | (2018.01) |
| *H04N 5/272* | (2006.01) |
| *H04N 5/92* | (2006.01) |
| *A61B 5/01* | (2006.01) |
| *A61B 5/021* | (2006.01) |
| *A61B 5/024* | (2006.01) |
| *A61B 5/08* | (2006.01) |
| *A61B 5/145* | (2006.01) |

(52) U.S. Cl.
CPC ............ *G06F 16/51* (2019.01); *G16H 10/60* (2018.01); *G16H 15/00* (2018.01); *G16H 30/20* (2018.01); *G16H 30/40* (2018.01); *G16H 40/63* (2018.01); *G16H 50/30* (2018.01); *H04N 5/272* (2013.01); *H04N 5/9201* (2013.01); *A61B 5/01* (2013.01); *A61B 5/021* (2013.01); *A61B 5/024* (2013.01); *A61B 5/0816* (2013.01); *A61B 5/14542* (2013.01)

(58) Field of Classification Search
CPC .... A61B 5/14542; G16H 10/60; G16H 15/00; G16H 30/20; G16H 30/40; G16H 40/63; G16H 50/30; G06F 16/51; G01S 7/52053; G01S 15/8906; H04N 5/272; H04N 5/9201

See application file for complete search history.

(56) References Cited

U.S. PATENT DOCUMENTS

| | | |
|---|---|---|
| 2006/0058660 A1 | 3/2006 | Sandy et al. |
| 2006/0119621 A1 | 6/2006 | Krier |
| 2007/0041660 A1* | 2/2007 | Mahesh ................. G16Z 99/00 |
| | | 382/294 |
| 2008/0012960 A1* | 1/2008 | Uchiyama ............ H04N 1/2112 |
| | | 348/231.2 |
| 2008/0263048 A1* | 10/2008 | Wise ...................... G06Q 10/10 |
| | | 707/999.009 |
| 2010/0189313 A1* | 7/2010 | Prokoski ................ A61B 5/015 |
| | | 382/118 |
| 2011/0137169 A1 | 6/2011 | Akaki et al. |
| 2014/0108053 A1 | 4/2014 | Akaki et al. |
| 2014/0143064 A1* | 5/2014 | Tran ...................... G16H 40/67 |
| | | 705/14.66 |
| 2014/0275832 A1* | 9/2014 | Muehlsteff ........... A61B 5/7207 |
| | | 600/301 |
| 2017/0000462 A1 | 1/2017 | Washburn et al. |
| 2017/0238842 A1* | 8/2017 | Jacquel ................ A61B 5/0205 |
| 2018/0296188 A1 | 10/2018 | Oura et al. |
| 2018/0353160 A1 | 12/2018 | Oura et al. |

FOREIGN PATENT DOCUMENTS

| | | |
|---|---|---|
| JP | 2017-86664 A | 5/2017 |
| JP | 2017-104534 A | 6/2017 |

OTHER PUBLICATIONS

International Written Opinion dated Oct. 18, 2019 issued by the International Searching Authority in counterpart International Application No. PCT/JP2019/029477 (PCT/ISA/237).
Communication issued Jul. 19, 2022 by the Japanese Patent Office in Japanese Patent Application No. 2018-149817.

* cited by examiner (A)

(B)

(C)

PHYSIOLOGICAL INFORMATION MEASUREMENT APPARATUS AND PHYSIOLOGICAL INFORMATION SYSTEM

CROSS-REFERENCE TO RELATED APPLICATIONS

This application is a National Phase Entry of PCT International Application No. PCT/JP2019/029477, filed on Jul. 26, 2019, which claims priority to Japanese Patent Application No. 2018-149817 filed on Aug. 9, 2018, the contents of all of which are incorporated herein by reference in their entirety.

TECHNICAL FIELD

The presently disclosed subject matter relates to a physiological information measurement apparatus and a physiological information system.

BACKGROUND ART

As information for knowing the condition of a subject, various vital signs (blood pressure, body temperature, respiration, heart rate, arterial oxygen saturation, and the like) are widely used. An ultrasonic inspection apparatus is used for knowing the internal condition of the chest, abdomen, or the like of a subject. Image information relating to the facial color of a subject and image information relating to a measurement portion of an ultrasonic diagnosis apparatus are also useful.

In recent years, there have been proposed techniques for simultaneously performing measurement of vital signs and ultrasonic diagnosis. For example, Patent Document 1 discloses a patient monitor (physiological information measurement apparatus) which switches between a first mode of displaying a screen which contains information of vital signs and a second mode of displaying a screen which contains an ultrasonic screen.

CITATION LIST

Patent Literature

PTL 1: JP-A-2017-86664

SUMMARY OF INVENTION

Technical Problem

The patient monitor of Patent Document 1 displays both information of vital signs and a captured image (ultrasonic image). There is a case where a medical person wants to store a captured image at treatment in order to check the condition of the subject under treatment later. In this case, if information of vital signs were also stored in a recognizable manner in addition to the captured image, the condition of the subject can be known more easily.

However, Patent Document 1 is silent about storing a captured image and fails to suggest referring to information of vital signs at a timing of an imaging operation.

This issue is relevant not only the case where the captured image is an ultrasonic image and also in a case where a patient monitor can be connected to a camera, for example.

The presently disclosed subject matter has been made in view of the above-described circumstances. An aspect of the presently disclosed subject matter provides a physiological information measurement apparatus which can be connected to an imaging device, and in which both information of a vital sign and a captured image at an image recording timing can be referred to, and a physiological information system including the physiological information measurement apparatus.

Solution to Problem

According to an aspect of the presently disclosed subject matter, there is provided a physiological information measurement apparatus configured to acquire a vital sign that is based on a physiological signal of a subject, and a captured image or a signal for generating the captured image that is acquired from an imaging device. The physiological information measurement apparatus includes:

a storage unit configured to store therein an electronic file; and a control unit configured to display at least one of the captured image and information of the vital sign on a display unit, wherein at an image recording timing when an image recording instruction is provided, the control unit stores both the captured image and the information of the vital sign in the storage unit in an image format.

The physiological information measurement apparatus acquires information of a vital sign that is based on the physiological signal of the subject, and the captured image or the signal for generating the captured image that is acquired from the imaging device. The control unit displays at least one of the captured image and the information of the vital sign on the display unit. The control unit stores both the captured image and the information of the vital sign in the storage unit in an image format at the timing (image recording timing) when the image recording instruction is provided. Since the captured image and information of the vital sign at the image recording timing are recorded as images, a user can refer to these information to know more accurately the condition of the subject.

Accordingly, the presently disclosed subject matter can provide a physiological information measurement apparatus which can be connected to an imaging device, and in which both information of a vital sign and a captured image at an image recording timing can be referred to, and a physiological information system including the physiological information measurement apparatus.

DESCRIPTION OF EMBODIMENTS

First Embodiment

Figure 1:
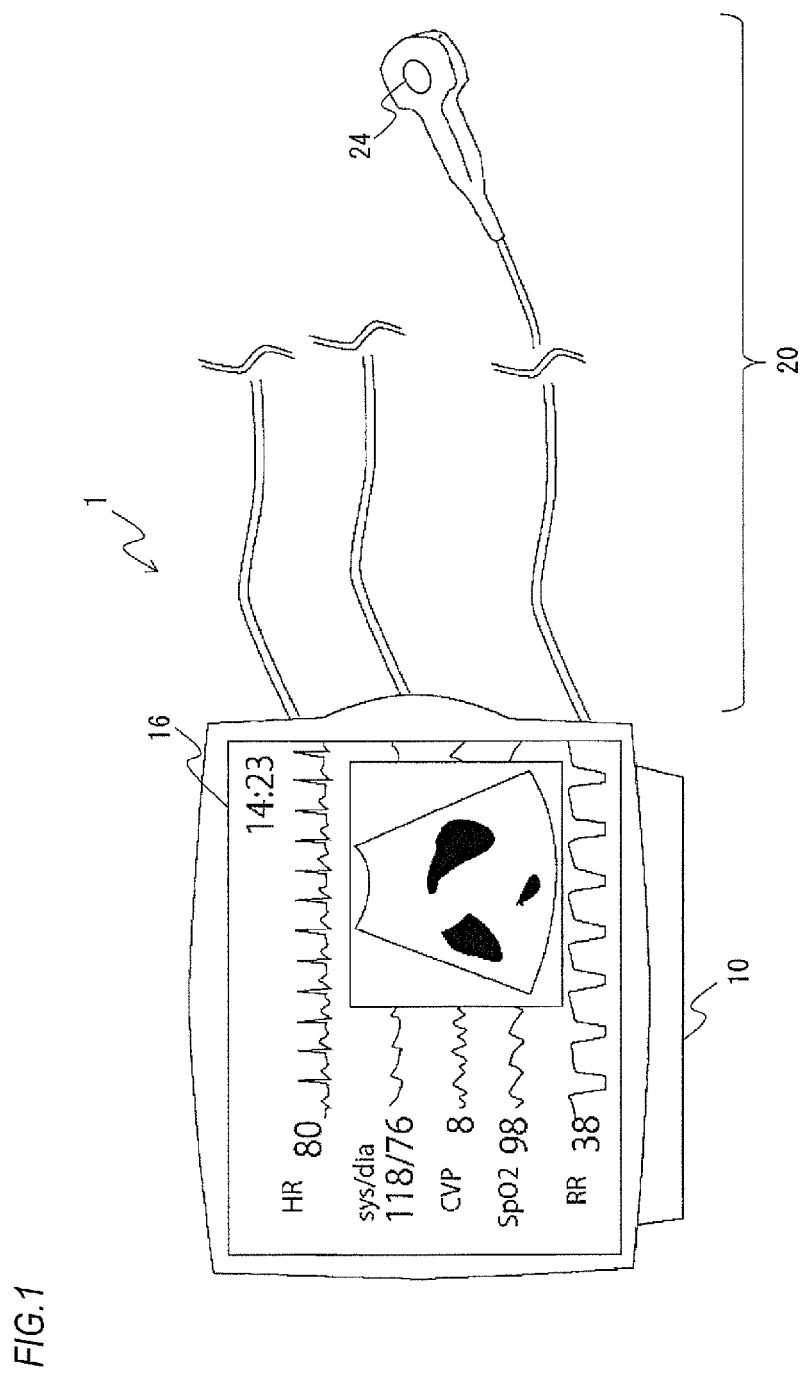
FIG. 1 illustrates the external configuration of a physiological information system according to a first embodiment.

Hereafter, embodiments of the presently disclosed subject matter will be described with reference to the drawings. FIG. 1 is a schematic view illustrating the external configuration of a physiological information measurement system 1 according to a first embodiment. The physiological information measurement system 1 may include a physiological information measurement apparatus 10 and an ultrasonic probe 20. Although not illustrated, the physiological information measurement apparatus 10 is appropriately connected also to sensors 30 (described later).

The physiological information measurement apparatus 10 measures various vital signs based on physiological signals which are acquired from various sensors 30 (described later with reference to FIG. 2) attached to a subject. The sensors 30 attached to the subject are various sensors used for measuring vital signs. For example, the sensors 30 may include: a cuff used for blood pressure measurement; electrodes (disposal electrodes; clip electrodes, and the like) used for electrocardiogram measurement, and the like; an SpO2 probe; a mask for respiration measurement; and the like. The vital signs which are the measurement targets may be, for example, the blood pressure, the body temperature, the respiration rate, the arterial oxygen saturation, an electrocardiogram, and the heart rate, and also information such as brain waves and an electromyogram.

The physiological information measurement apparatus 10 encompasses a concept including a bedside monitor, a medical telemeter, a defibrillator having a function of electrocardiogram measurement or the like, an electrocardiograph, an electroencephalograph, an electromyograph, and the like. That is, the physiological information measurement apparatus 10 may be interpreted as various medical apparatuses which measure vital signs. The physiological information measurement apparatus 10 may be an apparatus having a portable size. In the following, the description will be made while it is assumed that the physiological information measurement apparatus 10 is a so-called bedside monitor as an example.

The physiological information measurement apparatus 10 may include connection ports (so-called connector jacks) which are configured to be connected to the various sensors 30. The physiological information measurement apparatus 10 can be connected to an imaging device for generating a captured image. In the embodiment, the imaging device is the ultrasonic probe 20. That is, in the embodiment, the captured image which is acquired by the imaging device is an ultrasonic image which is captured based on a reflected wave of an ultrasonic wave transmitted onto the subject by the ultrasonic probe 20. The imaging device may be attached to the physiological information measurement apparatus 10 or configured to be detachable therefrom.

For example, the connection between the ultrasonic probe 20 and the physiological information measurement apparatus 10 may be performed through a Universal Serial Bus (USB) or another appropriate connector. In the ultrasonic probe 20, a probe 21 (described later) is contacted with (or placed in the vicinity of) the living body of the subject, so as to acquire an ultrasonic image of the interior of the living body of the subject. The ultrasonic probe 20 is a device having a weight and size that can be held by the user (mainly, the doctor) and having a form in which a cable is connected to a probe head of a usual ultrasonic diagnosis apparatus.

In the physiological information measurement apparatus 10, the ultrasonic image acquired by the ultrasonic probe 20 can be displayed on a display unit 16.

The ultrasonic probe 20 may have any form as long as the ultrasonic probe 20 is connectable to the physiological information measurement apparatus 10. That is, the ultrasonic probe 20 may communicate data with the physiological information measurement apparatus 10 through not only wired connection as illustrated but also wireless connection.

As illustrated, the ultrasonic probe 20 may include a button (operation unit) 24 on a case. The button 24 is an example of an interface which is configured to be operated in order to record an ultrasonic image at capturing as a still image (or a moving image) and may be configured in another form (for example, a knob or a trackwheel).

Figure 2:
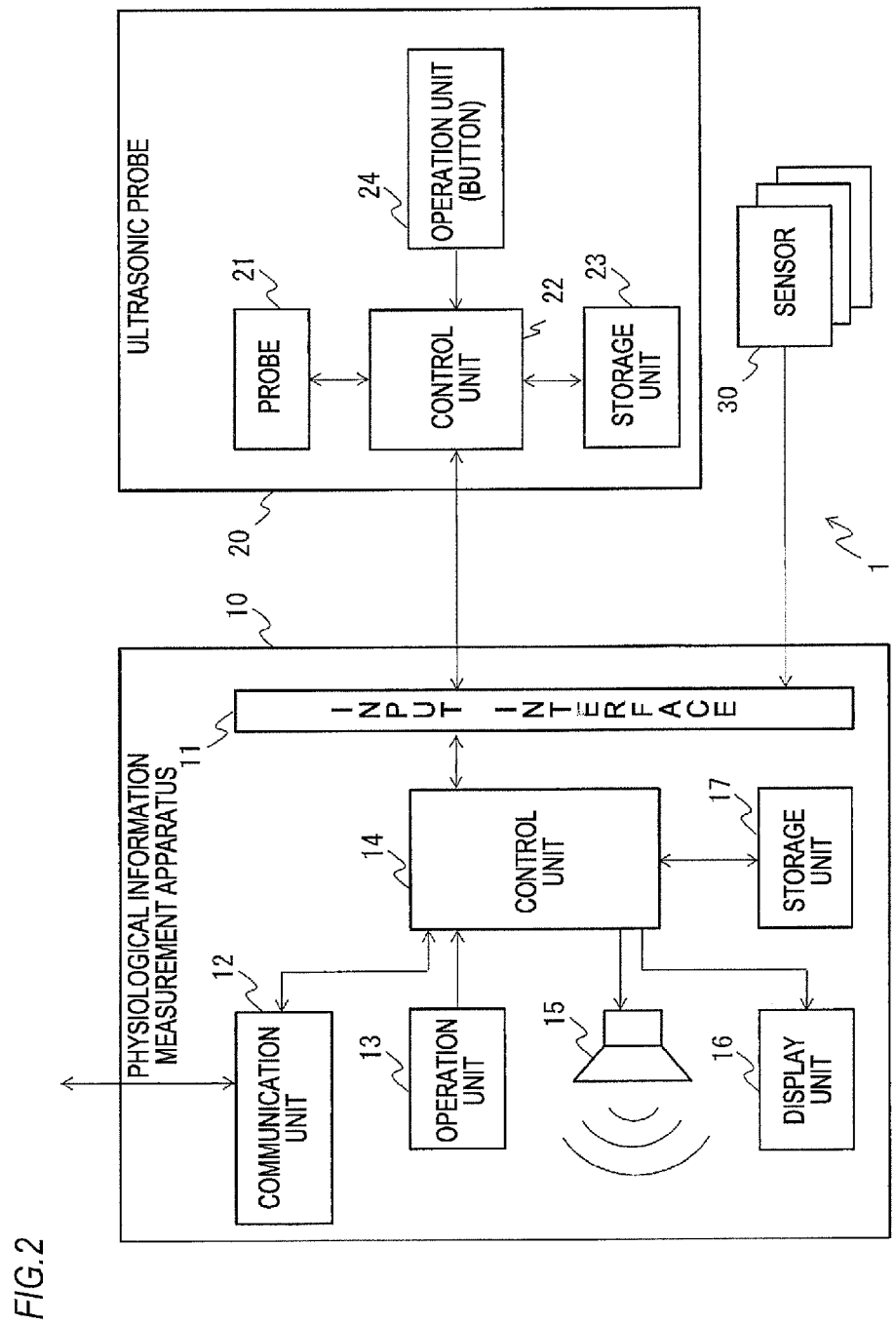
FIG. 2 is a block diagram illustrating the internal configuration of the physiological information system 1 according to the first embodiment.

The internal configuration of the physiological information system 1 will be described with reference to FIG. 2. The physiological information measurement apparatus 10 may include an input interface 11, a communication unit 12, an operation unit 13, a control unit 14, a speaker 15, the display unit 16, and a storage unit 17. Although not illustrated, the physiological information measurement apparatus 10 may appropriately include a Read Only Memory (ROM), a Random Access Memory (RAM), an internal power supply, and the like. The physiological information measurement apparatus 10 may further include an internal clock (not illustrated) which measures the time.

The input interface 11 may include the above-described connection ports, their peripheral circuits, and the like. The input interface 11 supplies signals which are received from the sensors 30 and the ultrasonic probe 20, to the control unit 14. The input interface 11 transmits a signal from the physiological information measurement apparatus 10 to the sensors 30 or the ultrasonic probe 20.

The communication unit 12 communicates data with other apparatuses (for example, a central monitor in the same hospital). For example, the communication unit 12 may be any form as long as the communication unit 12 complies with a communication standard for a wireless Local Area Network (LAN) or the like. The communication unit 12 may perform a communication process through a wired cable.

The user (mainly, the doctor) performs an input operation on the physiological information measurement apparatus 10 through the operation unit 13. The operation unit 13 may include buttons, knobs, rotary selector, keys, or the like which are disposed on, for example, the case of the physiological information measurement apparatus 10. An input through the operation unit 13 is supplied to the control unit 14.

The speaker 15 outputs various notification sounds such as an alarm. The speaker 15 performs notification in accordance with the control by the control unit 14.

The display unit 16 may include a display device which is disposed on the case of the physiological information measurement apparatus 10, a peripheral circuit thereof, and the like. The display unit 16 displays measurement waveforms and measurement values of various vital signs, an ultrasonic image, and the like in accordance with the control by the control unit 14. The display unit 16 is not always necessary to be integrated with the physiological information measurement apparatus 10, and may be configured by a display device which can be connected to the physiological information measurement apparatus 10 through a USB cable or the like.

The operation unit 13 and the display unit 16 may be integrated with each other (such as that similar to a so-called touch panel).

The storage unit 17 stores various programs (including system software and various kinds of application software), and data (including measurement data such as measurement values and waveforms of vital signs, the date and time when measurement data are measured, electronic files (for example, a first image file which will be described later), recording timing of an ultrasonic image, and the like) that are to be used by the control unit 14. The storage unit 17 may include, for example, a hard disk drive which is incorporated in the physiological information measurement apparatus 10. Various data are written as electronic files in the storage unit 17 (specifically, a file system of the storage unit 17). The storage unit 17 is not limited to a device which is incorporated in the physiological information measurement apparatus 10 and may be attachable to and detachable from the physiological information measurement apparatus 10 (for example, a Universal Serial Bus (USB) memory which is attachable to and detachable from the physiological information measurement apparatus 10).

The function of the control unit 14 is realized by a Central Processing Unit (CPU, not illustrated) and its peripheral circuits in the physiological information measurement apparatus 10. The control unit 14 appropriately reads programs or data from the storage unit 17. The control unit 14 appropriately writes data in the storage unit 17.

The control unit 14 acquires physiological signals from the sensors 30 (for example, an SpO2 probe, a blood pressure cuff, and a mask) through the input interface 11, and performs various processes (such as A/D conversion and filtering process) on the physiological signals, so as to acquire information (waveforms and measurement values of the blood pressure, the SpO2, the body temperature, and the like) of vital signs, control alarm sounding which is based on the information of the vital signs, and the like. The control unit 14 controls the display unit 16 to display the information (the waveforms and the measurement values) of the vital signs thereon.

Figure 3:
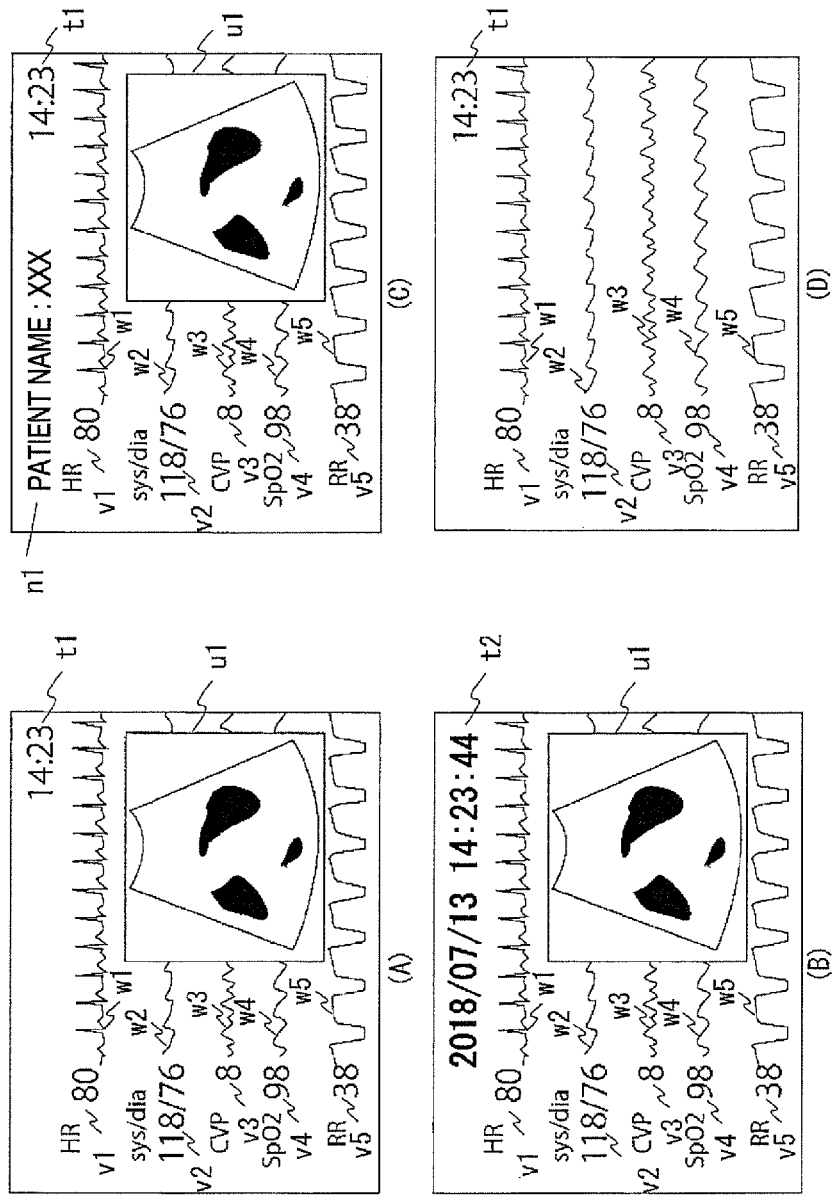
FIG. 3 illustrates examples of a first image file stored in a physiological information measurement apparatus 10 according to the first embodiment.
Figure 4:
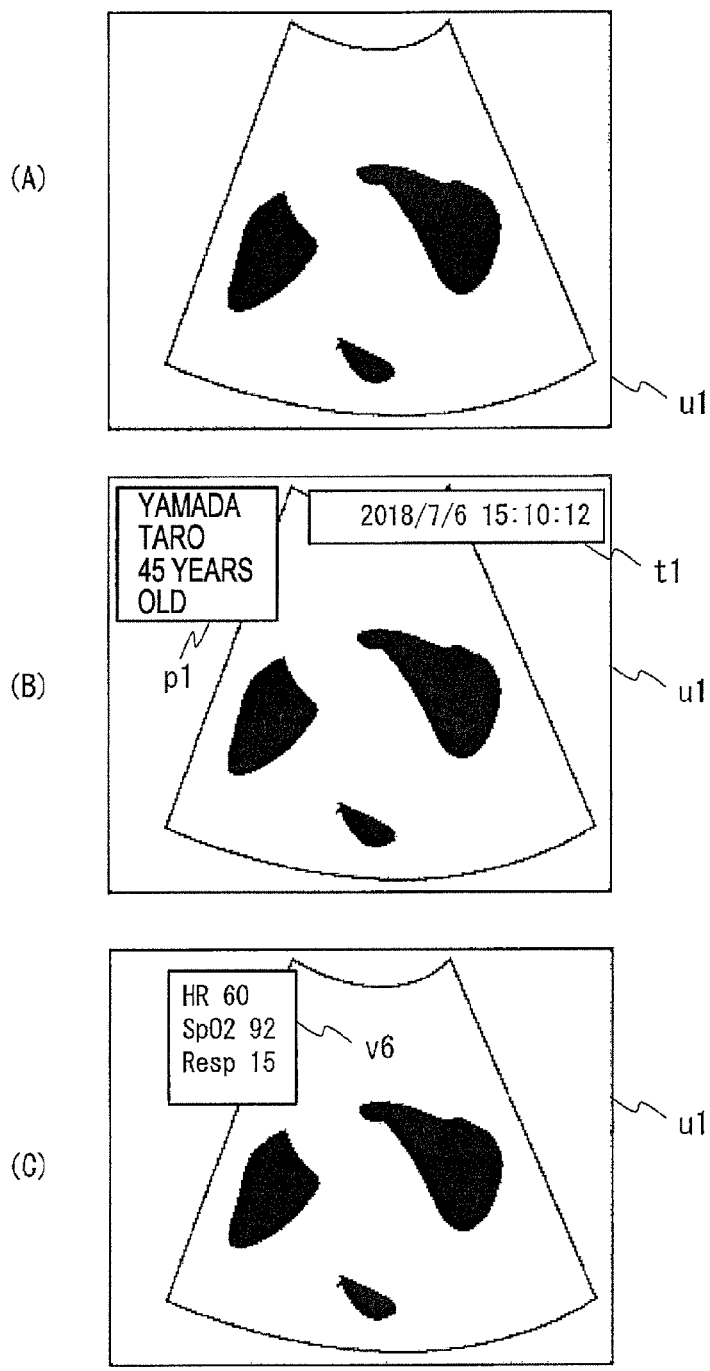
FIG. 4 illustrates examples of a second image file stored in the physiological information measurement apparatus 10 according to the first embodiment.
Figure 5:
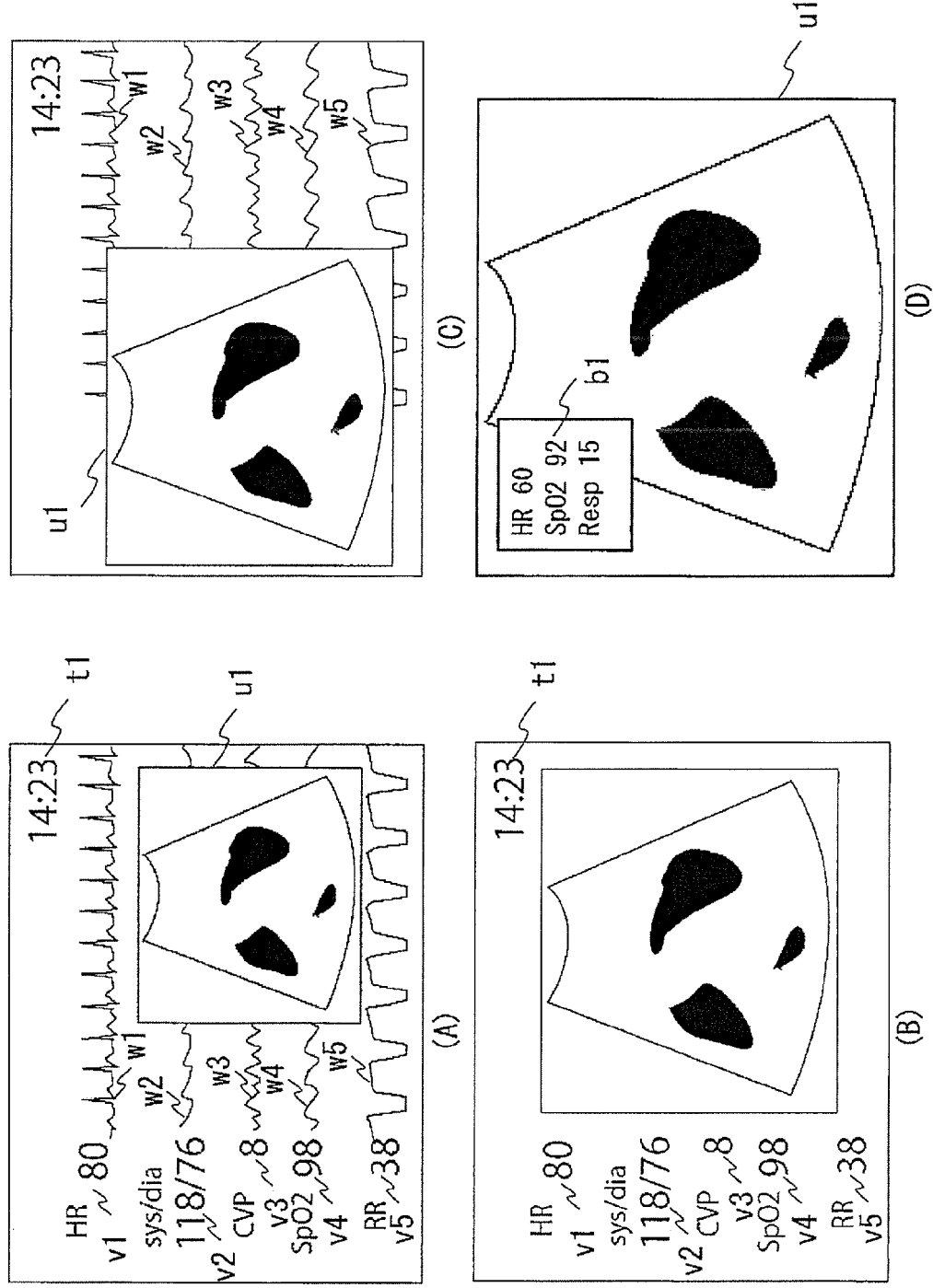
FIG. 5 illustrates examples of a combined image file stored in the physiological information measurement apparatus 10 according to the first embodiment.

At a timing (image recording timing) when an image recording instruction is provided, the control unit 14 stores both the ultrasonic image (captured image) and information of the vital signs at this timing, in the storage unit 17 in an image format. Here, the image recording timing may be the instance when the user performs an operation intended to record an image (the image recording instruction), or a timing after a lapse of a predetermined time period (for example, a time period of one to three seconds from the instance, or a time period from recognition of an input signal indicating the image recording instruction to starting of the image recording process). The storage in the image format will be described later with reference to FIGS. 3 to 5. The image recording instruction is executed in response to an operation of the button 24 of the ultrasonic probe 20 or that of the operation unit 13 which is performed by the user. The image recording instruction is an instruction intended to record a still image or a moving image as an image file and is thought of as a trigger of the start of image recording. When the button 24 is operated, the ultrasonic probe 20 transmits an image recording instruction signal to the control unit 14. The generation and storage of an image file will be described later with reference to FIG. 3.

The control unit 14 writes various setting information (for example, the subject name, the age, sex and previous medical history of the subject, and setting inherent to the apparatus, such as display settings) into a setting file or the like in the storage unit 17, and reads data from the setting file or the like in accordance with an operation performed on the operation unit 13.

Then, the ultrasonic probe 20 will be described. The ultrasonic probe 20 has a so-called probe-like shape. The ultrasonic probe 20 may include the probe 21, a control unit 22, a storage unit 23, and the operation unit 24. The ultrasonic probe 20 may be a device which operates with a power supply from the physiological information measurement apparatus 10 or includes therein an internal power supply.

The probe 21 is contacted with (or placed in the vicinity of) the living body of the subject and transmits an ultrasonic wave to the living body. The probe 21 receives an ultrasonic wave (reflected wave) reflected from the living body of the subject. The probe 21 supplies the received ultrasonic wave to the control unit 22.

The type of the probe 21 is not particularly limited. That is, the probe 21 may be of one of the convex type, the sector type, the linear type, and other types. The operation unit 24 (a knob, a button, an operation wheel, or the like) may be disposed on a case of the probe 21. The user operates the operation unit 24 to change the setting and the like of the probe 21.

The storage unit 23 stores various software programs (including system software and various kinds of application software), and data (including history and set values of the ultrasonic image, and the like) which are used by the control unit 22. The storage unit 23 may include, for example, a hard disk drive which is incorporated in the ultrasonic probe 20.

The function of the control unit 22 is realized by a Central Processing Unit (CPU) and its peripheral circuits which are not illustrated. The control unit 22 appropriately reads programs or data from the storage unit 23. The control unit 22 appropriately writes data in the storage unit 23.

The control unit 22 performs various settings of the probe 21, and reading and imaging of the received signal acquired by the probe 21. Specifically, the control unit 22 performs: setting of the beam forming of the probe 21; formation of an ultrasonic reception beam from the received reflection; various signal processings (mode signal processing, CF signal processing, Doppler signal processing, and the like) on the ultrasonic reception beam; formation of an ultrasonic image by scan processing; detection of an error of the probe 21; and the like. The control unit 22 transmits the ultrasonic image which is formed from the reception signal of the probe 21, to the physiological information measurement apparatus 10. When the function of acquiring an ultrasonic image is ON, the control unit 22 regularly generates an ultrasonic image, and transmits the ultrasonic image to the physiological information measurement apparatus 10. Alternatively, the control unit 22 may transfer the signal of the reflected wave which is acquired by the probe 21, as it is to the physiological information measurement apparatus 10. In this alternative, the control unit 14 performs a process of generating an ultrasonic image based on the signal of the reflected wave.

Next, cooperative operations between the ultrasonic probe 20 and the physiological information measurement apparatus 10 will be described. The control unit 22 of the ultrasonic probe 20 transmits the ultrasonic image or the signal of the reflected wave to the physiological information measurement apparatus 10. In the case where the signal of the reflected wave is received, the control unit 14 of the physiological information measurement apparatus 10 performs a process of converting the signal to an ultrasonic image. The control unit 14 of the physiological information measurement apparatus 10 further receives the physiological signals from the sensors 30 and analyzes the physiological signals, so as to calculate information (measurement waveforms and measurement values) of various vital signs (heart rate, body temperature, CVP, SpO2, respiration rate, and the like) in real time.

The control unit 14 displays the calculated information (measurement values and measurement waveforms) of the vital signs in real time on the display unit 16. In the example of FIG. 1, the measurement values and waveforms of the heart rate/electrocardiogram (HR), the blood pressures (sys/dia), the CVP, the SpO2, and the respiration rate (RR) are displayed in real time on the display unit 16. In addition, the control unit 14 displays the ultrasonic image (captured image) in real time on the display unit 16. In the example of FIG. 1, a screen in which the ultrasonic image is superimposed on the information (waveforms and measurement values) of various vital signs is displayed on the display unit 16. The control unit 14 can display only one of the information of vital signs and the ultrasonic image on the display unit 16, in accordance with the user setting. That is, the control unit 14 controls the display unit 16 so as to display at least one the information of vital signs and the captured image (ultrasonic image).

The operation in the case where, in the display state of FIG. 1, the image recording instruction (an operation on the button of the ultrasonic probe 20, or that on the operation unit 13) is provided will be described. When the image recording instruction is provided, the signal indicating the image recording instruction is supplied to the control unit 14. Here, the image recording instruction is an instruction instructing storage of an image in a form of a still image or a moving image.

At the image recording timing when the image recording instruction is provided, the control unit 14 stores both the information of vital signs and the ultrasonic image (captured image) in the storage unit 17 in one of following <1> and <2> modes.

<1> A first image file containing the information of vital signs, and a second image file containing the ultrasonic image (captured image) are generated and stored in the storage unit 17.

<2> A combined image file in which the information of vital signs and the ultrasonic image (captured image) are combined with each other is generated and stored in the storage unit 17.

Hereinafter, <1> and <2> modes will be described in detail.

First, the <1> mode will be described. At the timing (image recording timing) when the image recording instruction is provided, the control unit 14 generates the second image file which will be described later, and an image file (first image file) containing the information of vital signs (at least one of the waveform and the measurement value). In the following description, it is assumed that the generated image file is a still image, and examples of the image file will be described with reference to FIG. 3.

For example, the control unit 14 generates a screen captured image of a screen indicating the information of vital signs (measurement waveforms or measurement values) and ultrasonic image that are displayed in real time. The method of generating a screen captured image (an image which is identical with a displayed image) may be realized by the function same as or similar to the method that is performed in a usual computer apparatus. The control unit 14 stores the screen captured image as the first image file in the storage unit 17 (FIG. 3(A)). In the first image file (FIG. 3(A)), measurement values v1 to v5 of vital signs, measurement waveforms w1 to w5 of the vital signs, an ultrasonic image ul, and time information t1 are displayed, which constitute the same or similar screen as that which is illustrated in FIG. 1.

The control unit 14 may generate an image file indicating a screen in which partial correction or information addition is applied to the contents of the displayed screen. As illustrated in FIG. 3(B), for example, the control unit 14 may generate the first image file indicating a screen in which the time information t1 in the screen that is being displayed is replaced with detailed time information t2 in which information of the year, the month, the day, and the second is added. The control unit 14 may acquire the time information t2 by using a time information acquisition method which is realized in a usual computer system.

As illustrated in FIG. 3(C), the control unit 14 may generate an image file indicating a screen in which, in addition to the screen that is being displayed, information that is read out from the storage unit 17 (for example, information that is read out from a database or setting file in the storage unit 17) is displayed. In the example of FIG. 3(C), the control unit 14 generates a screen on which information of the name of the subject is displayed in the screen captured image, as the first image file, and stores the file in the storage unit 17.

The control unit 14 may stores a screen which, as illustrated in FIG. 3(D), contains the information of vital signs (measurement waveforms and measurement values), but in which the ultrasonic image is removed, as the first image file in the storage unit 17. The first image file illustrated in FIG. 3(D) contains the measurement values v1 to v5 of vital signs, the measurement waveforms w1 to w5 of the vital signs, and the time information t1, but does not contain the ultrasonic image ul.

FIGS. 3(A) to 3(D) illustrate mere examples, and the image file (first image file) which is generated by the control unit 14 may not be an image that is generated based on screen capturing. The control unit 14 may generate any type of image file and stores the file in the storage unit 17 as long as the image contains information of vital signs at the image recording timing.

In the above description, although the first image file is assumed to be a still image file, the first image file may be a moving image file. In this case, the control unit 14 may store a moving image as a file containing information of vital signs (measurement waveforms or measurement values) for a predetermined period of time (for example, 10 seconds) after the image recording timing.

In addition to the above-described image file (first image file), the control unit 14 stores an image file (second image file) containing the ultrasonic image at the image recording timing in the storage unit 17. Hereinafter, examples of the second image file will be described with reference to FIGS. 4(A) to 4(C).

For example, the control unit 14 may store an image (FIG. 4(A)) in which the ultrasonic image is displayed in a large screen, in the storage unit 17 as the second image file. As illustrated in FIG. 4(A), the ultrasonic image ul at the image recording timing is stored in the storage unit 17 as the second image file.

The control unit 14 may store a screen in which various kinds of information such as subject information (for example, the name, age, and sex of the subject), date and time information, and information of various settings (for example, the mode and depth of an ultrasonic wave) at the image recording timing are superimposed on the image in which the ultrasonic image is displayed on a large screen, in the storage unit 17 as the second image file. In the example of FIG. 4(B), the second image file in which subject information (the name, age, and sex of the subject) p1 and date and time information t1 are superimposed on the ultrasonic image ul is stored in the storage unit 17.

The control unit 14 may store a screen in which numerical information of various vital signs at the image recording timing is superimposed on the image in which the ultrasonic image is displayed on a large screen, in the storage unit 17 as the second image file. In the example of FIG. 4(C), the second image file in which measurement information v6 of various vital signs such as the heart rate (HR), the SpO2, and the respiration rate (Resp) is superimposed on the ultrasonic image ul is stored in the storage unit 17.

FIGS. 4(A) to 4(C) illustrate mere examples of the second image file. For example, an image file in which subject information, date and time information, and numerical information of vital signs are superimposed on an ultrasonic image, or that in which other information is further imposed may be stored. The second image file is not limited to a sill image file and may be a moving image file.

In the case where the first image file or the second image file is a moving image file, the following image acquisitions may be performed. In the case where the control unit 14 caches information of vital signs which is displayed on the display unit 16 in a predetermined preceding time before, in a memory that is not illustrated, the control unit 14 may store a moving image containing information (measurement waveforms or measurement values) of vital signs for a predetermined time period (for example, 10 seconds) before the image recording timing, as the first image file. In the same or similar manner, the control unit 14 may store a moving image containing information (measurement waveforms or measurement values) of vital signs for a predetermined time period (for example, from five seconds before the image recording timing to five seconds from the image recording timing) before and after the image recording timing, as the first image file. With respect to the second image file, the same or similar process is performed. That is, the control unit 14 may store a moving image containing an ultrasonic image for a predetermined time period before the image recording timing, as the second image file, or store a moving image containing an ultrasonic image for a predetermined time period before and after the image recording timing, as the second image file.

Next, the <2> mode (storage of combined image file) will be described. The control unit 14 generates one combined image file which contains both information of vital signs and an ultrasonic image (captured image), and stores the combined image file in the storage unit 17. Hereinafter, the combined image file will be described with reference to FIG. 5.

For example, the control unit 14 may generate a screen captured image of a screen on which information of vital signs (measurement waveforms or measurement values) and ultrasonic image that are displayed in real time, as a combined image file, and stores the combined image file in the storage unit 17 (FIG. 5(A)). In the same or similar manner as FIGS. 3(B) and 3(C), various kinds of information (for example, the date and time, and the name of the subject) may be superimposed on the screen captured image.

The control unit 14 may generate an image in which the screen that is displayed in real time is partially adjusted, as a combined image file. In the example of FIG. 5(B), the control unit 14 removes the measurement waveforms of vital signs and displays the ultrasonic image ul in the area for the measurement waveforms in an enlarged manner. That is, the control unit 14 generates a screen on which the measurement values v1 to v5 of the vital signs and the ultrasonic image ul are displayed, as a combined image file, and stores the combined image file in the storage unit 17.

In the same or similar manner, the control unit 14 may remove the measurement values of vital signs, generate a screen in which the ultrasonic image ul is displayed in the area for the measurement values in an enlarged manner, as a combined image file, and stores the combined image file in the storage unit 17 (FIG. 5(C)).

The control unit 14 may generate a screen in which information of vital signs is superimposed on an ultrasonic image, as a combined image file. For example, the control unit 14 may store a screen in which, as illustrated in FIG. 5(D), measurement values b1 of vital signs are superimposed on the ultrasonic image ul at the image recording timing, as a combined image file in the storage unit 17.

Although examples of the combined image file have been described above, the combined image file may have another form as long as the combined image file contains both information (measurement waveforms or measurement values) of vital signs and an ultrasonic image.

The above-described two modes <1> and <2> may be switchable by a user operation of the operation unit 13.

In addition to the above-described storages of image information (the above-described processes of <1> and <2> modes), the control unit 14 may acquire a first non-image file indicating information (waveforms and measurement values) of vital signs at the image recording timing, and stores the file in the storage unit 17. Hereinafter, the description will be made while it is assumed that the above-described <1> mode is performed. In the case where the <2> mode is performed, the process is performed in a similar manner.

The first non-image file is a file containing information in which information (waveforms and measurement values) of vital signs is expressed as character strings or numerical values. The first non-image file may have a format of a CSV file or an XML file. The first non-image file may be preferably associated with the first image file by, for example, writing the file name of the first image file.

In addition to the first image file, the control unit 14 may acquire a second non-image file containing non-image information at the image recording timing, and store the file in the storage unit 17. For example, the second non-image file contains at least one of subject information, date and time information, apparatus information, and setting information. The subject information is information containing, for example, the name, sex, age, and previous medical history of the subject. The date and time information is information of the date and time of the image recording timing. The apparatus information is information of the model number and the like of the physiological information measurement apparatus 10. The setting information is information indicating the ultrasonic imaging mode and the like. The second non-image file may be preferably associated with the first image file by writing the file name of the first image file.

The first and second non-image files are not necessarily different files and may be generated as one file.

Hereinafter, a storage example of the first image file, the second image file, the first non-image file, and the second non-image file in the file system of the storage unit 17 will be described with reference to FIG. 6. In the example, it is assumed that the image recording is performed at 14:23:44 of July 13 of the 30th year of the Heisei era, and 9:24:51 of July 17 of the 30th year of the Heisei era.

In the case where an image recording instruction is provided at 14:23:44 of July 13 of the 30th year of the Heisei era, the control unit 14 generates a folder corresponding to the data and time. Then, the control unit 14 refers to the information of vital signs and ultrasonic image at the data and time, and generates the first image file (for example, FIG. 3(A)), the second image file (for example, FIG. 4(A)), the first non-image file, and the second non-image file. Here, the control unit 14 sets the file name of each of the files, i.e., the data and time (H300713_142344) of the image recording timing as the prefix of the file. The control unit 14 operates folders such that the storage destinations of the files are the same folder. In the example, the control unit 14 stores the files in the folder named "/echo/subjectA/H300713_142344".

In the same or similar manner, in the case where an image recording instruction is provided at 9:24:51 of July 17 of the 30th year of the Heisei era, the control unit 14 generates a folder corresponding to the data and time. Then, the control unit 14 refers to information of vital signs and ultrasonic image at the data and time, and generates the first image file (for example, FIG. 3(A)), the second image file (for example, FIG. 4(A)), the first non-image file, and the second non-image file. Here, the control unit 14 sets the file name of each of the files, i.e., the data and time (H300717_092451) of the image recording timing as the prefix of the file. The control unit 14 operates the folders such that the storage destinations of the files are the same folder. In the example, the control unit 14 stores the files in the folder named "/echo/subjectA/H300717_092451".

In the case where the storage destinations of the first and second image files are the same folder on a file system, the relationship between the first and second image files can be known at a glance. In the case where the storage destinations of the first image file and the first non-image file are the same folder on the file system, the relationship between the first image file and the first non-image file can be known at a glance.

Since the file names of the first and second image files have the common portion, the relationship between the files can be known at a glance. The same or similar is applicable to the file names of the first image file and the first non-image file. The common portion (common character string or number string) of file names are not necessarily information relating to the data and time and may be determined in accordance with a predetermined rule.

Figure 6:
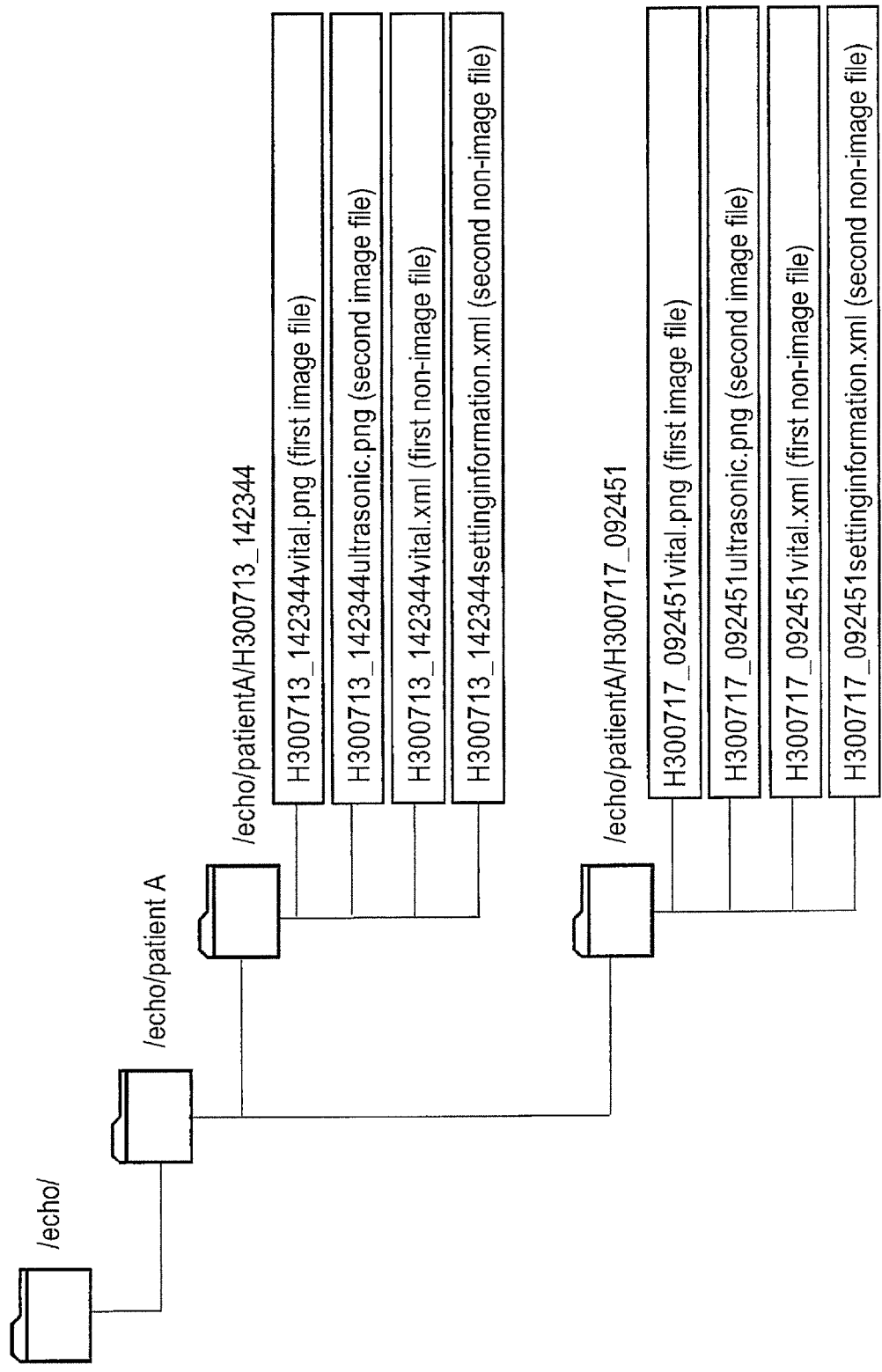
FIG. 6 illustrates a storage example of image files in a file system of a storage unit 17 according to the first embodiment.

Although, in the example of FIG. 6, a folder is prepared for each image recording timing, the process is not limited thereto. For example, the control unit 14 may sequentially store the first image file and the like which are prepared in a folder corresponding to the subject A.

Then, effects of the physiological information measurement apparatus 10 of the above-described embodiment will be described. The physiological information measurement apparatus 10 acquires information of vital signs based on physiological signals of the subject received from the sensors 30, and an ultrasonic image (an example of the captured image) or a signal of the reflected wave for generating the ultrasonic image that is acquired from the ultrasonic probe 20 (an example of the imaging device). The control unit 14 displays at least one of the ultrasonic image and the information of vital signs on the display unit 16. The control unit 14 stores both the ultrasonic image and the information of the vital signs in the storage unit 17 in an image format at the timing (image recording timing) when the image recording instruction is provided. Since the ultrasonic image and information of the vital sign at the image recording timing are recorded as images, the user can refer to these information and know more accurately the condition of the subject.

Here, both the first image file containing the information of vital signs, and the second image file containing the ultrasonic image are stored (the <1> mode), and therefore, each of the information of vital signs, and the ultrasonic image can be easily known.

In the case where the first image file relates to a screen containing the ultrasonic image (FIGS. 3(A) to 3(C)), the states of the ultrasonic image and vital signs at the image recording timing can be known from one file. In the case where the first image file is an image file generated by screen capturing, particularly, information the amount of which is identical with that of information viewed at treatment (or inspection) can be referred at a later time.

In the case where the first image file is an image file of a screen in which the ultrasonic image is superimposed on a screen on which measurement waveforms of vital signs are displayed (FIGS. 3(A) to 3(C)), and the second image file is relevant to the ultrasonic image (or an image obtained by superimposing various information on the ultrasonic image) (FIGS. 4(A) to 4(C)), it is possible to refer to both information based on the ultrasonic image, and information based on the information of vital signs. Therefore, the user can refer more accurately to the condition of the subject at the image recoding timing.

The control unit 14 may calculate the information of vital signs, display the information in real time on the display unit 16, and also display the ultrasonic image in real time on the display unit 16 (FIG. 1). Therefore, it is possible to know both the information even during inspection or treatment of the subject, and hence highly accurate inspection and treatment can be realized.

Second Embodiment

According to a second embodiment, the physiological information measurement apparatus 10 is connected to a camera 40 in place of the ultrasonic probe 20. That is, in the second embodiment, imaging device is the camera 40, and the captured image is a peripheral image which is obtained by capturing an image of the periphery. Hereinafter, description will be made with focusing on differences from the first embodiment. In the following description, the processing units which are indicated by names and reference numerals that are same as or similar to those used in the first embodiment perform functions same as or similar to those of Embodiment 1 unless particularly described (the same shall apply to a third embodiment described later).

Figure 7:
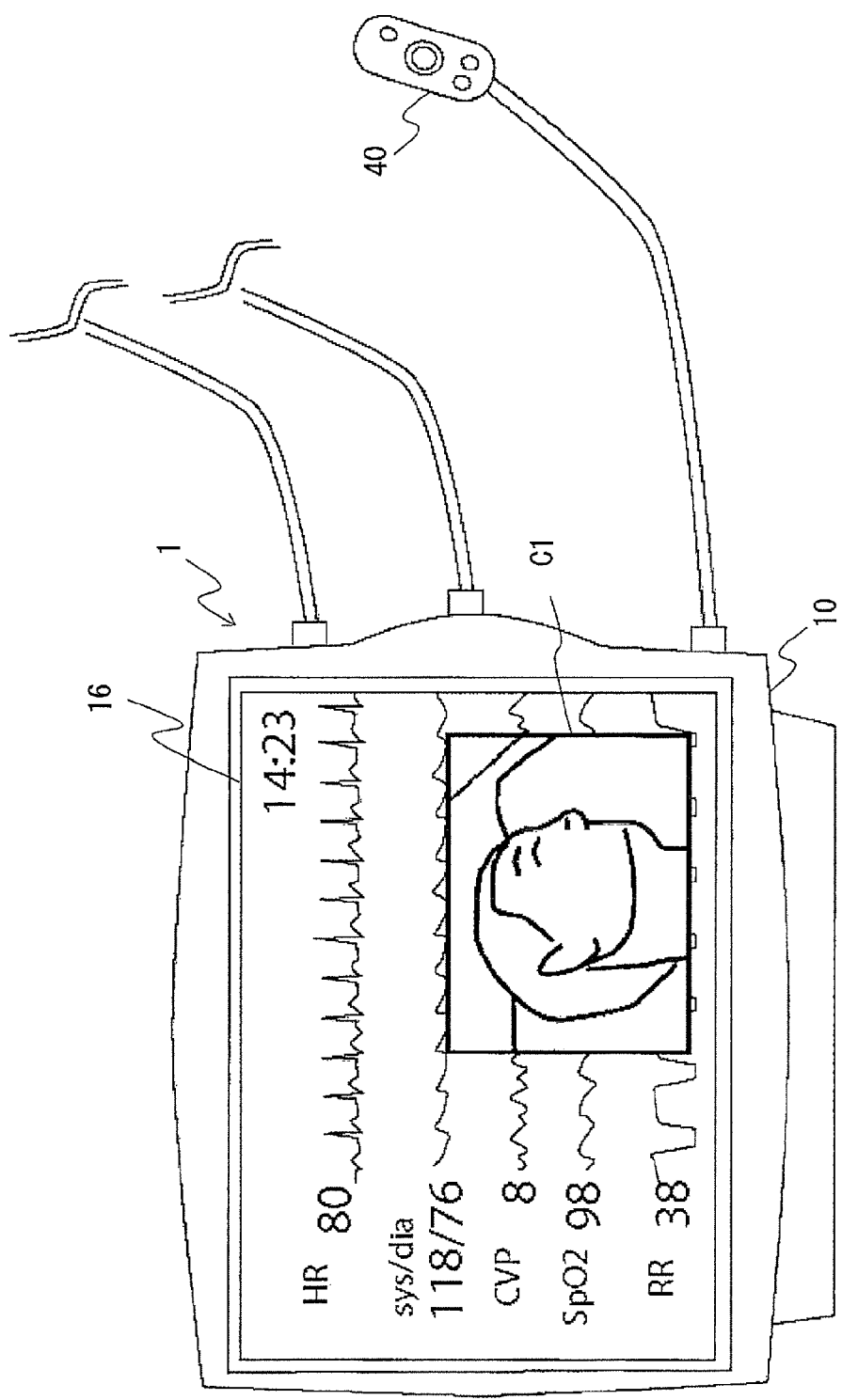
FIG. 7 illustrates the external configuration of a physiological information system 1 according to a second embodiment.

FIG. 7 illustrates the external configuration of a physiological information system 1 according to the second embodiment. As illustrated, the camera 40 is connected to the physiological information measurement apparatus 10 through a cable. Alternatively, the camera 40 may be wirelessly connected to the physiological information measurement apparatus 10 (that is, a signal can be communicated via a wireless signal). In the physiological information measurement apparatus 10, the peripheral image acquired by the camera 40 is displayed on the display unit 16. In the example of FIG. 7, an image in which the face of the subject is captured by the camera 40 is displayed on the display unit 16 together with information (measurement values and measurement waveforms) of vital signs.

Figure 8:
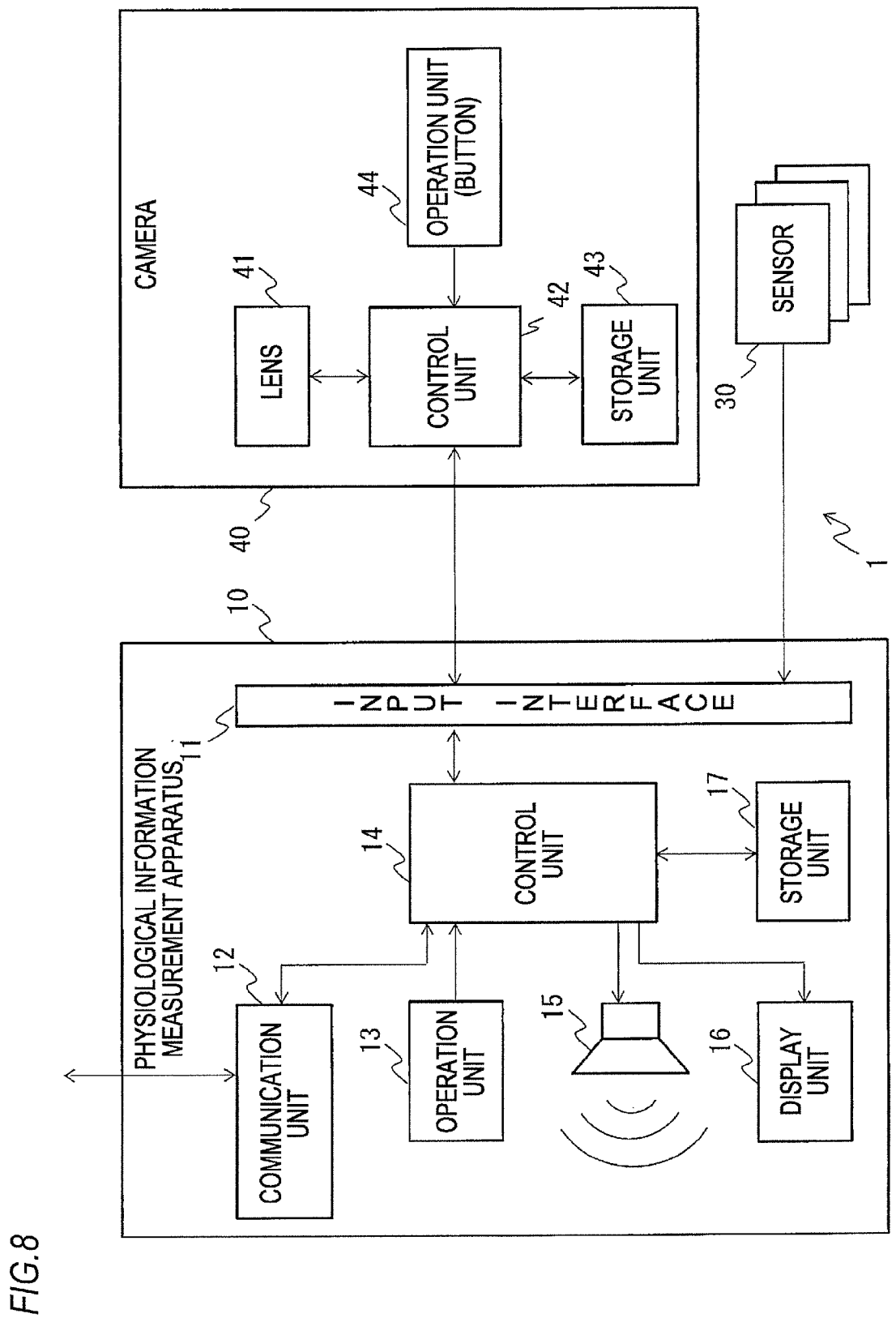
FIG. 8 is a block diagram illustrating the internal configuration of the physiological information system 1 according to the second embodiment.

FIG. 8 is a block diagram illustrating the internal configuration of the physiological information system 1 according to the second embodiment. Unlike the configuration of FIG. 2, the physiological information measurement apparatus 10 may include the camera 40 in place of the ultrasonic probe 20.

The camera 40 may include a lens 41, a control unit 42, a storage unit 43, and an operation unit 44. It is assumed that, although not illustrated, the camera 40 may include processing units which are provided in a usual digital still camera, for example, various peripheral circuits, a diaphragm, and a photometric system such as a CMOS.

The operation unit 44 is an interface which receives an input of the image recording instruction by the subject, and may include, for example, a button or a knob. An object light beam which enters through the lens 41 is converted to a light detection signal by the photometric system which is not illustrated. The light detection signal is converted into a digital signal by an A/D converter or the like which is not illustrated.

The control unit 42 performs various digital processes (the contrast adjustment and the like) on the digital signal to generate a peripheral image. The storage unit 43 stores various programs and data which are necessary in the operation of the control unit 42, and various data are written into the storage unit by the control unit 42. In the case where the camera function is ON, the control unit 42 regularly generates the peripheral image from the light detection signal (digital signal) and transmits the image to the physiological information measurement apparatus 10. Alternatively, the control unit 42 may provide the light detection signal (the signal is preferably a digital signal, but may be an analog signal) as it is to the physiological information measurement apparatus 10, and the physiological information measurement apparatus 10 may generate the peripheral image.

The control unit 14 of the physiological information measurement apparatus 10 displays the peripheral image acquired from the camera 40, and the information (measurement values and measurement waveforms) of vital signs based on the physiological signals acquired from the sensors 30, in real time on the display unit 16. In the example of FIG. 7, a peripheral image Cl which is obtained by capturing the vicinity of the face of the subject is displayed on the display unit 16 together with the information (measurement values and measurement waveforms) of vital signs.

Figure 9:
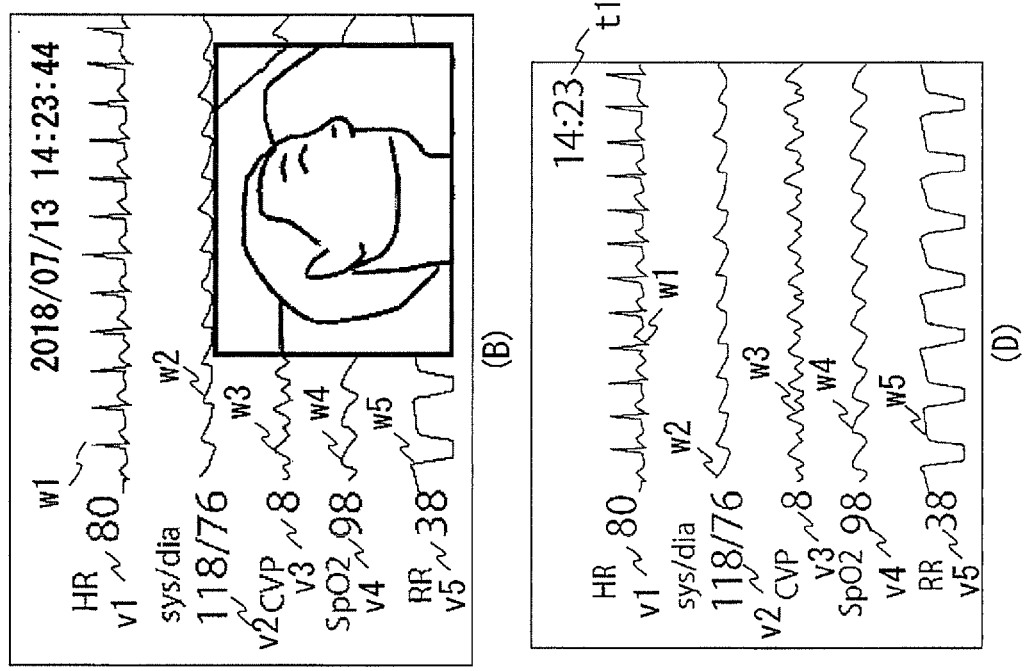
FIG. 9 illustrates examples of a first image file stored in a physiological information measurement apparatus 10 according to the second embodiment.
Figure 9:
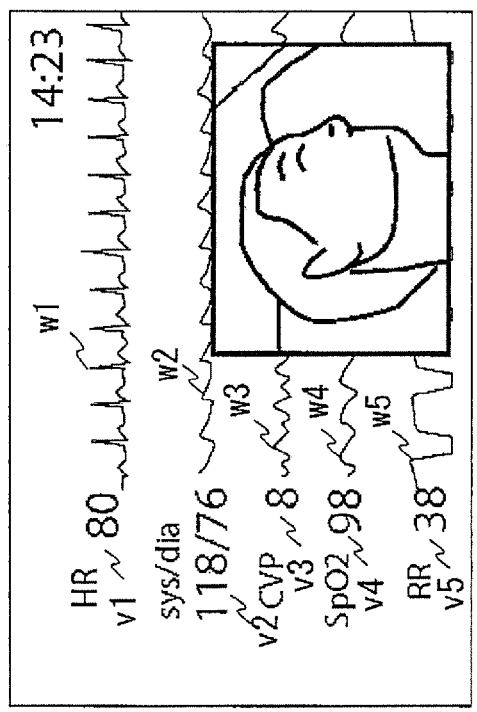
Figure 9:
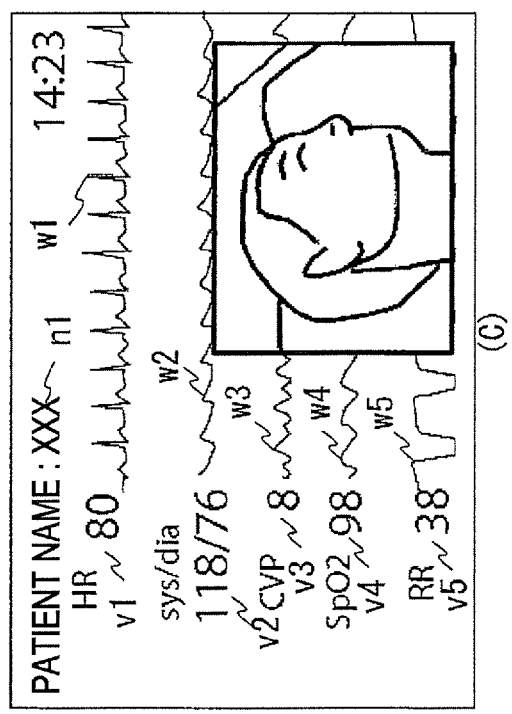
Figure 10:
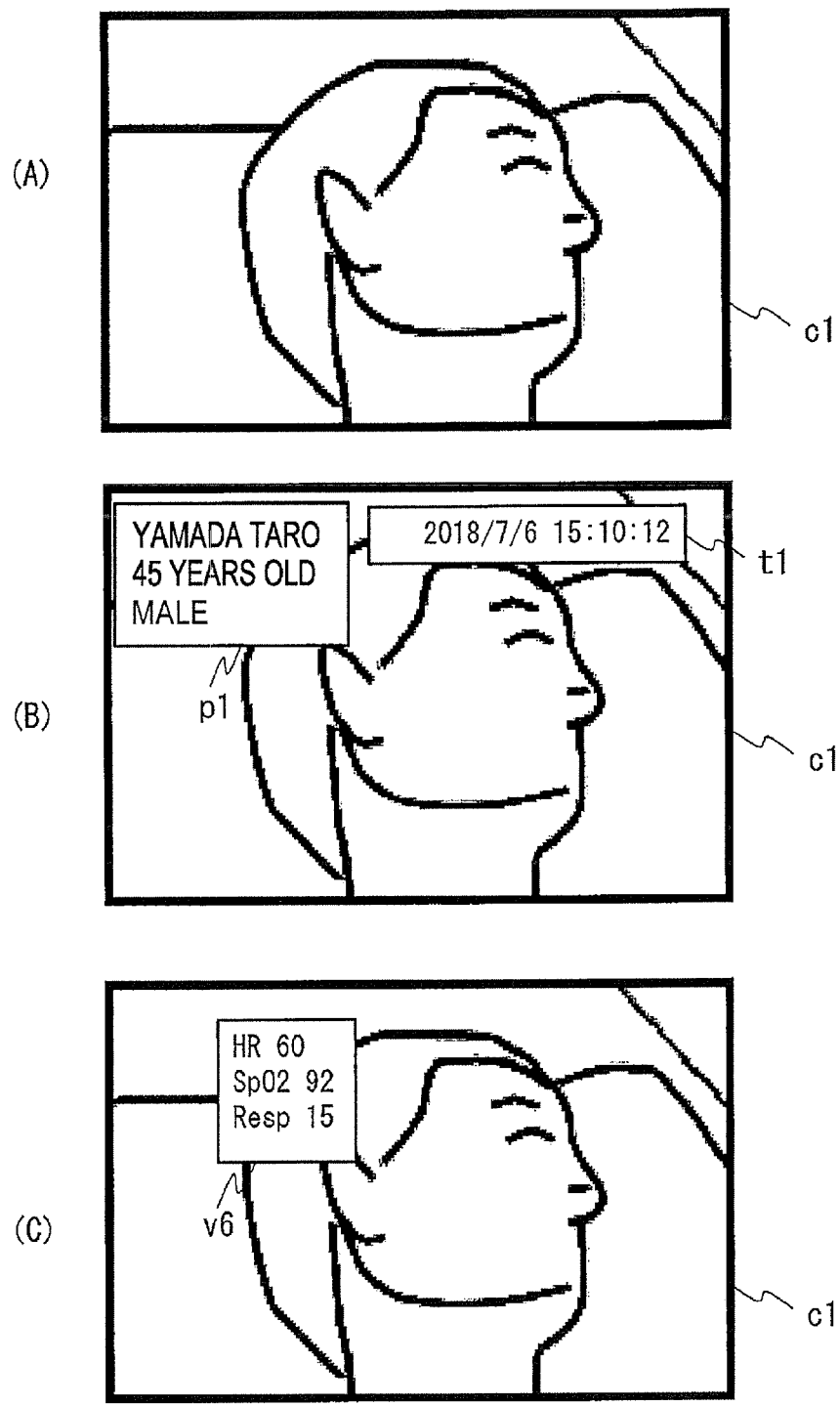
FIG. 10 illustrates examples of a second image file stored in the physiological information measurement apparatus 10 according to the second embodiment.

The operation in the case where the image recording instruction (an operation on the button of the camera 40, or that on the operation unit 13) is provided in the state of FIG. 7 will be described. The image recording instruction may be realized by an operation in which the control unit 42 transmits the recording instruction signal to the physiological information measurement apparatus 10 in response to, for example, an operation of the operation unit 44, or realized by generation of the recording instruction signal in response to an operation performed on the operation unit 13. When the image recording instruction is provided, the control unit 14 stores the information of the vital signs and the peripheral image (captured image) in the storage unit 17 in an image format by one of the above-described <1> and <2> modes. The following operations are substantially identical with those in the first embodiment, and therefore, only the operations corresponding to the <1> mode and an image file will be described with reference to FIGS. 9 and 10.

The control unit 14 generates a screen capture screen of a screen on which, for example, the information (measurement values and measurement waveforms) of the vital signs and the peripheral image are displayed, and stores the screen capture screen in the storage unit 17 as the first image file (FIG. 9(A)). The control unit 14 may store a screen in which a part of the screen capture screen is replaced with other information (for example, a screen in which time information is replaced with detailed date and time information), in the storage unit 17 as the first image file (FIG. 9(B)).

The control unit 14 may store a screen in which various information (for example, subject information (the name and the like of the subject)) that are read out from the storage unit 17 are superimposed on the screen capture screen, in the storage unit 17 as the first image file (FIG. 9(C)). The control unit 14 may store a screen which, as illustrated in FIG. 9(D), contains the information of vital signs (measurement waveforms and measurement values), but in which the ultrasonic image is removed, as the first image file in the storage unit 17.

In addition to the above-described image file (first image file), the control unit 14 stores an image file (second image file) containing the peripheral image at the image recording timing, in the storage unit 17. Hereinafter, examples of the second image file will be described with reference to FIGS. 10(A) to 10(C).

The control unit 14 may store a screen (FIG. 10(A)) in which the peripheral image is displayed in a large screen, in the storage unit 17 as the second image file. The control unit 14 may store a screen (FIG. 10(B)) in which the subject information and the date and time information are superimposed on the peripheral image, in the storage unit 17 as the second image file. The control unit 14 may store a screen in which the measurement information v6 of various vital signs at the image recording time is superimposed on the peripheral image, in the storage unit 17 as the second image file.

FIGS. 10(A) to 10(C) illustrate mere examples of the second image file. The second image file may be the peripheral image itself, or an image relating to a screen on which the peripheral image and various information are displayed.

Effects of the physiological information measurement apparatus 10 of the second embodiment are substantially identical with those of the first embodiment. That is, at the timing (image recording timing) when the image recording instruction is provided, the control unit 14 stores both the peripheral image (an example of the captured image) and the information of the vital signs, in the storage unit 17 in an image format. Since the peripheral image and information of the vital sign at the image recording timing are recorded as images, the user can refer to these information, and know more accurately the condition of the subject at the image recording timing.

Third Embodiment

According to a third embodiment, the physiological information measurement apparatus 10 is connected to an imaging device in which the ultrasonic probe 20 and the camera 40 are integrated with each other. Hereinafter, description will be made with focusing on differences from the first and second embodiments.

Figure 11:
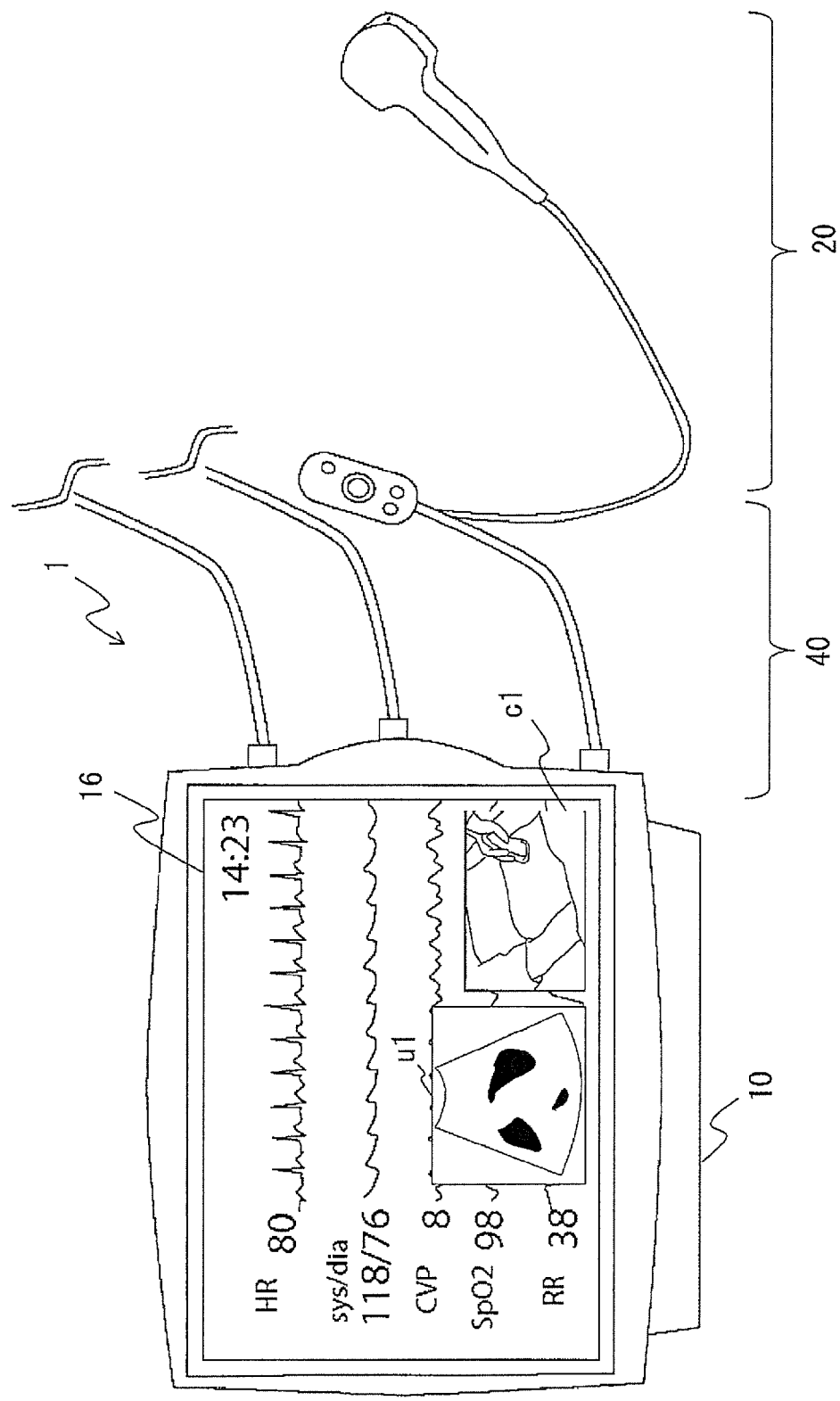
FIG. 11 illustrates the external configuration of a physiological information system 1 according to a third embodiment.

FIG. 11 is an external diagram illustrating the configuration of a physiological information system 1 according to the third embodiment. The physiological information system 1 may include the physiological information measurement apparatus 10, the ultrasonic probe 20, and the camera 40. The physiological information measurement apparatus 10 of the third embodiment is connected to two imaging devices (the ultrasonic probe 20 and the camera 40), and the captured image may include both the ultrasonic image and the peripheral image. Although not illustrated, the physiological information measurement apparatus 10 is appropriately connected also to the sensors 30 (described later).

The physiological information measurement apparatus 10 and the camera 40 are connected to each other through a cable, and the camera 40 and the ultrasonic probe 20 are connected to each other through another cable. The communication connections among these apparatuses may be realized by wireless connection.

The configurations and functions of the ultrasonic probe 20 and the camera 40 are substantially identical with those in the first or second embodiment. The ultrasonic image (or the signal of the reflected wave) acquired by the ultrasonic probe 20, and the peripheral image are supplied to the physiological information measurement apparatus 10.

The control unit 14 displays the information (measurement values and measurement waveforms) of the vital signs calculated based on physiological signals that are acquired from the sensors 30 (not illustrated in FIG. 11), in real time on the display unit 16. The control unit 14 displays both the ultrasonic image and the peripheral image on the display unit 16 in real time. In FIG. 11, a screen in which the ultrasonic image ul and a peripheral image cl are superimposed on the information (measurement values and measurement waveforms) of the vital signs is displayed on the display unit 16.

The operation in the case where the image recording instruction (an operation on the button of the camera 40, or that on the operation unit 13) is provided in the state of FIG. 11 will be described. When the image recording instruction is provided, the signal indicating the image recording instruction is supplied to the control unit 14.

Figure 12:
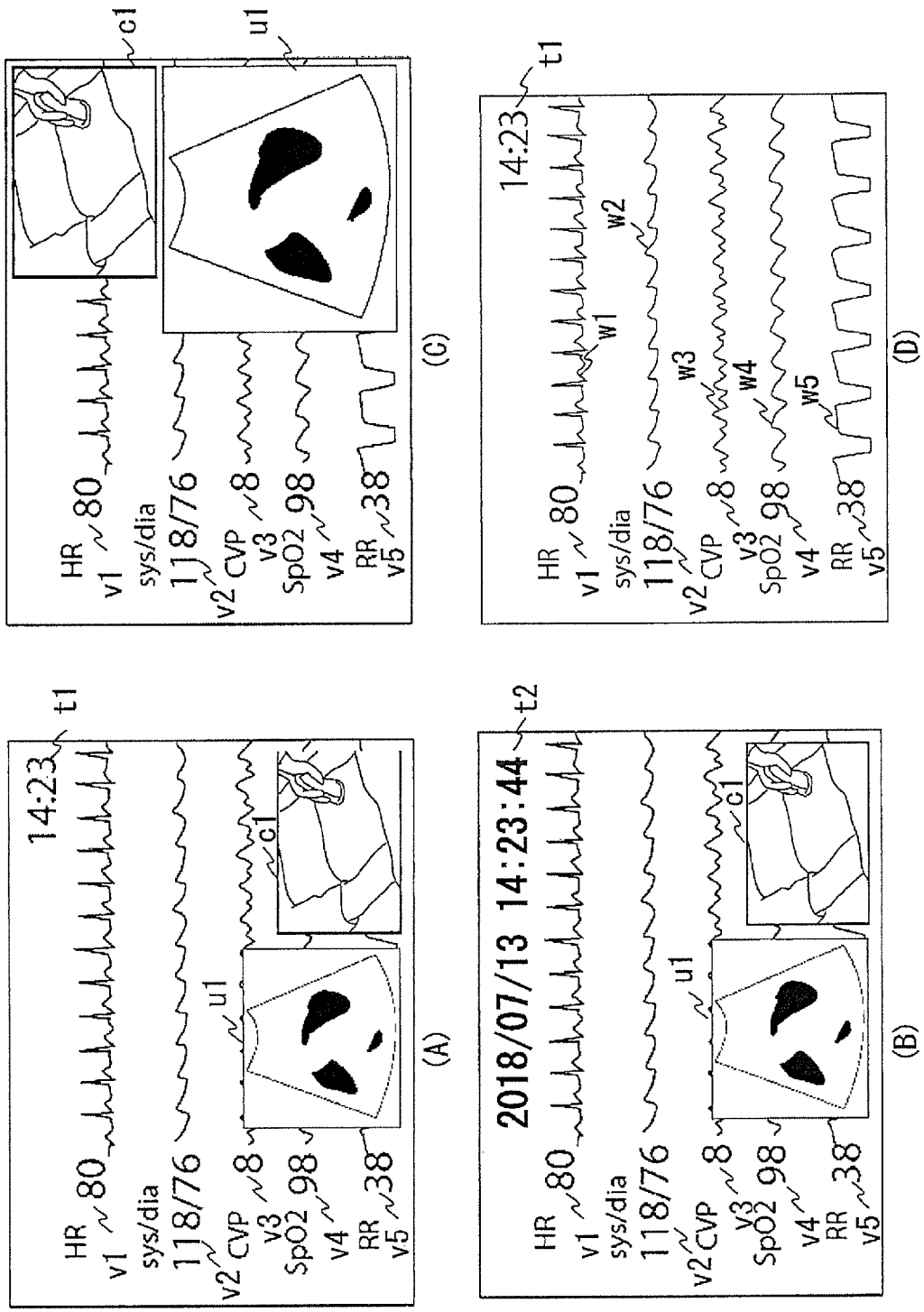
FIG. 12 illustrates examples of a first image file stored in a physiological information measurement apparatus 10 according to the third embodiment.
Figure 13:
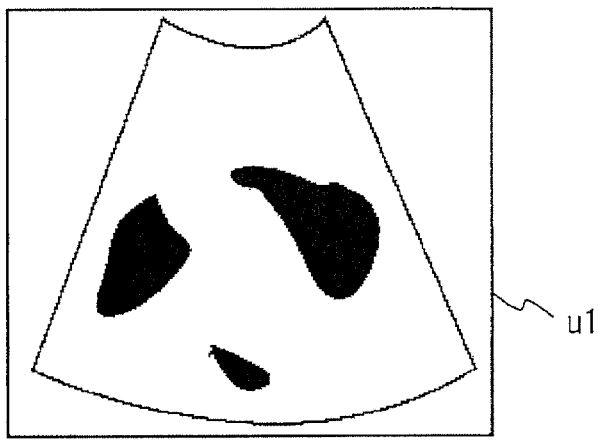
FIG. 13 illustrates examples of a second image file stored in the physiological information measurement apparatus 10 according to the third embodiment.
Figure 13:
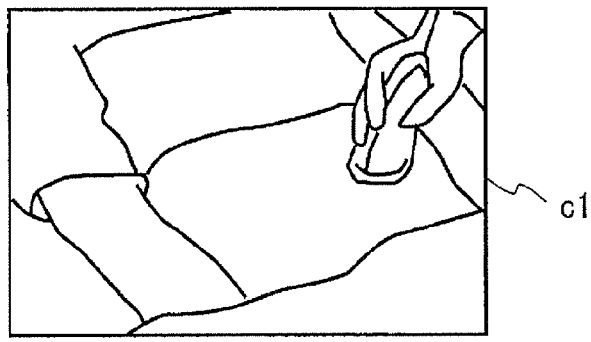
Figure 13:
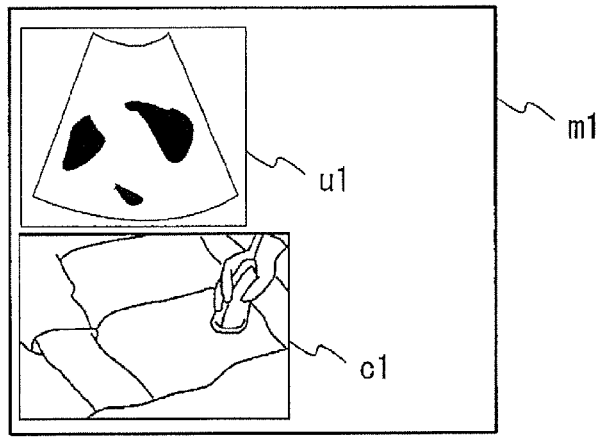

When the image recording instruction is provided, the control unit 14 stores the information of the vital signs, the ultrasonic image and the peripheral image in the storage unit 17 in an image format by one of the above-described <1> and <2> modes. The following operations are substantially identical with those in the first embodiment, and therefore, only the operations and image files corresponding to the <1> mode will be described with reference to FIGS. 12 and 13.

The control unit 14 generates a screen capture screen of a screen on which, for example, the information (measurement waveforms and measurement values) of the vital signs, the peripheral image, and the ultrasonic image are displayed, and stores the screen capture screen in the storage unit 17 as the first image file (FIG. 12(A)). The control unit 14 may store a screen in which a part of the screen capture screen is replaced with other information (for example, a screen in which time information is replaced with detailed date and time information), in the storage unit 17 as the first image file (FIG. 12(B)).

The control unit 14 may store a screen in which, for example, the peripheral image and the ultrasonic image are displayed at an enlarged manner while being superimposed on the information (measurement waveforms and measurement values) of the vital signs, in the storage unit 17 as the first image file (FIG. 12(C)). Since the first image file contains the information (measurement waveforms and measurement values) of the vital signs, the peripheral image, and the ultrasonic image as illustrated in FIGS. 12(A) to 12(C), it is possible to know more accurately the condition of the subject (and that of the periphery of the subject) at the image recording timing.

The control unit 14 may store a screen which, as illustrated in FIG. 12(D), contains the information of the vital signs (measurement waveforms and measurement values), but in which the ultrasonic image and the peripheral image are removed, as the first image file in the storage unit 17. That is, in the embodiment, the first image file may be of any type as long as the file contains information of vital signs.

In addition to the above-described image file (first image file), the control unit 14 stores an image file (second image file) containing at least one of the peripheral image and ultrasonic image at the image recording timing, in the storage unit 17. Hereinafter, examples of the second image file will be described with reference to FIGS. 13(A) to 13(C).

The control unit 14 may store a screen (FIG. 13(A)) on which the ultrasonic image is displayed in a large screen, in the storage unit 17 as the second image file. The control unit 14 may store a screen (FIG. 13(B)) on which the peripheral image is displayed in a large screen, in the storage unit 17 as the second image file. The control unit 14 may store a screen in which the ultrasonic image and the peripheral image are combined with each other, in the storage unit 17 as the second image file (FIG. 13(C)). Although not illustrated, the information (measurement values) of the vital signs and various information (the patient information and the date and time information) may be superimposed on each of the screens.

In the case where a combined image file is stored in the <2> mode, it is preferable that the combined image file is a screen on which, as illustrated in FIG. 12(A), information (measurement waveforms and measurement values) of vital signs, a peripheral image, and an ultrasonic image are displayed.

That is, the control unit 14 stores a combined image file which contains information of vital signs, a peripheral image, and an ultrasonic image, in the storage unit 17. This enables the condition of the subject (the conditions of the subject and the periphery of the subject) at the image recording time to be accurately known from simply one image file.

Although the presently disclosed subject matter has been specifically described based on the embodiments, the present invention is not limited to the above-described embodiments, and it is appreciated for the skilled person that various changes can be made without departing from the spirit of the presently disclosed subject matter.

The present application is based on Japanese Patent Application No. 2018-149817 filed on Aug. 9, 2018, the contents of which are incorporated herein by way of reference.

The invention claimed is:

1. A physiological information measurement apparatus configured to acquire a vital sign that is based on a physiological signal of a subject, and a captured image captured by an imaging device configured to capture a periphery of the subject, the physiological information measurement apparatus comprising:
a storage configured to store therein an electronic file; and
at least one processor configured to render the captured image and information of the vital sign at a time of capture of the captured image on a display,
wherein the imaging device is a camera, and an ultrasonic probe which are connected to the physiological information measurement apparatus, and
wherein the captured image contains a peripheral image which is obtained by capturing a vicinity of the subject and an ultrasonic image which is captured based on a reflected wave of an ultrasonic wave transmitted onto the subject by the ultrasonic probe,
wherein the at least one processor if further configured to render, on the display, an image in which the ultrasonic image and the peripheral image are superimposed on the information of the vital sign at the time of capture of the captured image, and
wherein at an image recording timing when an image recording instruction is provided, the at least one processor is further configured to generate and store, in the storage in an image format, at the time of capture of the captured image, the image in which the ultrasonic image and the peripheral image are superimposed on the information of the vital sign.

2. The physiological information measurement apparatus according to claim 1, wherein the at least one processor is further configured to:
analyze the physiological signal acquired by a sensor which is connected to the physiological information measurement apparatus;
calculate the information of the vital sign and render the information of the vital sign in real time on the display; and
acquire the captured image and render the captured image in real time on the display.

3. The physiological information measurement apparatus according to claim 1, wherein at the image recording timing, the at least one processor is further configured to:
generate a combined image file in which the captured image and the information of the vital sign are combined with each other; and
store the combined image file in the storage.

4. The physiological information measurement apparatus according to claim 1, wherein at the image recording timing, the at least one processor is further configured to:
acquire a first non-image file containing non-image information in which the information of the vital sign is expressed as a numerical value or a character string; and
store the first non-image file in the storage.

5. The physiological information measurement apparatus according to claim 1, wherein at the image recording timing, the at least one processor is further configured to:
acquire a second non-image file containing non-image information which contains at least one of subject information, time information, apparatus information, and setting information; and
store the second non-image file in the storage.

6. The physiological information measurement apparatus according to claim 1,
wherein the physiological information measurement apparatus is connected to the imaging device in which the ultrasonic probe and the camera are integrated with each other.

7. The physiological information measurement apparatus according to claim 1,
wherein the at least one processor is further configured to generate an image file which contains information of the subject read out from the storage and the at least one of the captured image and the information of the vital sign.

8. The physiological information measurement apparatus according to claim 1,
wherein the image recording timing includes a first image recording timing and a second image recording timing,
wherein the at least one processor is further configured to generate a first folder corresponding to the first image recording timing in the storage,
wherein the at least one processor is further configured to store a first file including the captured image and the information of the vital sign at the first image recording timing in the first folder,
wherein the at least one processor is further configured to generate a second folder corresponding to the second image recording timing and different from the first folder in the storage, and
wherein the at least one processor is further configured to store a second file including the captured image and the information of the vital sign at the second image recording timing in the second folder.

9. The physiological information measurement apparatus according to claim 1,
wherein the at least one processor is further configured to store both the captured image and the information of the vital sign in an image format of a still image or a moving image in the storage.

10. The physiological information measurement apparatus according to claim 1,
wherein the imaging device is further configured to capture an ultrasonic image that is captured based on a reflected wave of an ultrasonic wave transmitted onto the subject, and
wherein at an image recording timing when an image recording instruction is provided, the at least one processor is configured to store the ultrasonic image in the storage in an image format, in addition to the peripheral image and the information of the vital sign.

11. The physiological information measurement apparatus according to claim 1,
wherein at the image recording timing, the at least one processor is further configured to:
generate a first image file which contains the information of the vital sign and a second image file which contains the captured image; and
store the first image file and the second image file in the storage.

12. The physiological information measurement apparatus according to claim 2,
wherein the first image file is an image file relating to a screen in which the captured image is superimposed on the screen displaying a measurement waveform of the vital sign, and
wherein the second image file is an image file relating to the captured image or the screen in which various information are superimposed on the captured image.

13. The physiological information measurement apparatus according to claim 2, wherein the first image file is a file relating to screen capturing of a screen which is rendered on the display at the image recording timing.

14. The physiological information measurement apparatus according to claim 2, wherein the at least one processor is further configured to store the first image file and the second image file in a same folder of a file system in the storage.

15. The physiological information measurement apparatus according to claim 11, wherein the at least one processor is further configured to set a part of a file name of the first image file and a part of a file name of the second image file to be common to each other.

16. A physiological information system comprising:

an imaging device configured to capture a periphery of a subject; and a physiological information measurement apparatus configured to acquire a vital sign that is based on a physiological signal of the subject, and a captured image captured by the imaging device, the physiological information measurement apparatus comprising:

a storage configured to store therein an electronic file; and at least one processor configured to render the captured image and information of the vital sign at a time of capture of the captured image on a display, wherein the imaging device is a camera and an ultrasonic probe, which are connected to the physiological information measurement apparatus, and wherein the captured image contains a peripheral image obtained by capturing a vicinity of the subject and an ultrasonic image which is captured based on a reflected wave of an ultrasonic wave transmitted onto the subject by the ultrasonic probe, wherein the at least one processor is further configured to render, on the display, an image in which the ultrasonic image and the peripheral image are superimposed on the information of the vital sign at the time of capture of the captured image, and wherein at an xcording tir ne whe instruction is provided, the at least one processor is further configured to generate and store, in the storage in an image format, at the time of capture of the captured image, the image in which the ultrasonic image and the peripheral image are superimposed on the information of the vital sign.

* * * * *